United States Patent
Brand et al.

(10) Patent No.: US 10,881,817 B2
(45) Date of Patent: Jan. 5, 2021

(54) SECRETION LOOSENING AND COUGH SEGMENTING THERAPY

(71) Applicant: KONINKLIJKE PHILIPS N.V., Eindhoven (NL)

(72) Inventors: Maarten Leonardus Christian Brand, Murrysville, PA (US); Michael Edward Colbaugh, Level Green, PA (US); James Garsteck, Scottdale, PA (US); Wei Zhou, Shanghai (CN)

(73) Assignee: Koninklijke Philips N.V., Eindhoven (NL)

( * ) Notice: Subject to any disclaimer, the term of this patent is extended or adjusted under 35 U.S.C. 154(b) by 357 days.

(21) Appl. No.: 15/538,221

(22) PCT Filed: Dec. 16, 2015

(86) PCT No.: PCT/IB2015/059655
§ 371 (c)(1),
(2) Date: Jun. 21, 2017

(87) PCT Pub. No.: WO2016/103116
PCT Pub. Date: Jun. 30, 2016

(65) Prior Publication Data
US 2017/0368410 A1 Dec. 28, 2017

(30) Foreign Application Priority Data
Dec. 26, 2014 (WO) ............... PCT/CN2014/095098

(51) Int. Cl.
*A61M 16/00* (2006.01)
*A61B 5/08* (2006.01)
(Continued)

(52) U.S. Cl.
CPC ....... *A61M 16/0006* (2014.02); *A61B 5/0823* (2013.01); *A61M 16/0009* (2014.02);
(Continued)

(58) Field of Classification Search
CPC ............. A61M 16/00; A61M 16/0006; A61M 2205/502; A61M 16/0866; A61M 16/20;
(Continued)

(56) References Cited

U.S. PATENT DOCUMENTS 5,165,398 A    11/1992   Bird
6,702,769 B1 *  3/2004   Fowler-Hawkins ........................
                                            A61M 16/0006
                                                128/200.24

(Continued)

FOREIGN PATENT DOCUMENTS

EP       2737920 A1      6/2014
WO    WO2010058308 A2    5/2010
(Continued)

OTHER PUBLICATIONS

Compliance, pulmonary. (1999). In E. Hodgson, R. B. Mailman, & J. E. Chambers (Eds.), MacMillan dictionary of toxicology (2nd ed.). Basingstoke, UK: Macmillan Publishers Ltd. Retrieved from https://search.credoreference.com/content/entry/mactox/compliance_pulmonary/0?institutionId=743 (Year: 1999).*
(Continued)

*Primary Examiner* — David J. McCrosky
(74) *Attorney, Agent, or Firm* — Daniel H. Brean

(57) ABSTRACT

The present system (10) comprises a subject interface (22), a segmenter (12), a loosener (14), sensors (18), and computer processors (28). The segmenter is configured to selectively control gas flow through the subject interface to provide high amplitude pressure oscillations (44) during exhalation such that the high amplitude pressure oscillations aid cough productivity in the subject. The loosener controls gas flow through the subject interface to provide low amplitude pressure oscillations (43, 63) during inhalation (48, 68) and exhalation (49) such that the low amplitude pressure oscillations loosen respiratory secretions. The computer
(Continued)

processors detect trigger events based on the output signals such that the one or more trigger events include a loosening trigger event and a segmenting trigger event (66); and responsive to detecting the loosening trigger event, control the loosener to provide the low amplitude pressure oscillations, and, responsive to detecting the segmenting trigger event, control the segmenter to provide the high amplitude pressure oscillations.

20 Claims, 5 Drawing Sheets

(51) Int. Cl.
| | | |
|---|---|---|
| *A61M 16/20* | (2006.01) | |
| *A63B 24/00* | (2006.01) | |
| *A63B 23/18* | (2006.01) | |
| *A63B 71/06* | (2006.01) | |
| *A63B 21/00* | (2006.01) | |
| *A61B 5/00* | (2006.01) | |
| *A61B 5/091* | (2006.01) | |

(52) U.S. Cl.
CPC .... *A61M 16/0051* (2013.01); *A61M 16/0096* (2013.01); *A61M 16/024* (2017.08); *A61M 16/201* (2014.02); *A63B 23/18* (2013.01); *A63B 24/0087* (2013.01); *A61B 5/0816* (2013.01); *A61B 5/091* (2013.01); *A61B 5/4833* (2013.01); *A61M 16/202* (2014.02); *A61M 16/209* (2014.02); *A61M 2016/0015* (2013.01); *A61M 2016/0021* (2013.01); *A61M 2205/3584* (2013.01); *A61M 2205/3592* (2013.01); *A61M 2205/505* (2013.01); *A61M 2205/52* (2013.01); *A63B 21/00181* (2013.01); *A63B 71/0622* (2013.01); *A63B 2024/0071* (2013.01); *A63B 2024/0093* (2013.01); *A63B 2071/0625* (2013.01); *A63B 2071/0627* (2013.01); *A63B 2071/0655* (2013.01); *A63B 2071/0683* (2013.01); *A63B 2220/30* (2013.01); *A63B 2220/40* (2013.01); *A63B 2220/56* (2013.01); *A63B 2220/64* (2013.01); *A63B 2220/833* (2013.01); *A63B 2225/01* (2013.01); *A63B 2225/50* (2013.01); *A63B 2225/74* (2020.08); *A63B 2230/431* (2013.01); *A63B 2230/505* (2013.01)

(58) Field of Classification Search
CPC .......... A61M 16/1055; A61M 16/0205; A61M 2016/0021; A61M 2016/003; A61M 2016/0033; A61M 2205/3584; A61M 2205/52; A61M 2205/583; A61M 16/0003; A61M 16/0012; A61M 16/0057; A61M 16/0066; A61M 16/0072; A61M 16/0075; A61M 16/0096; A61M 16/021; A61M 16/022; A61M 16/024; A61M 16/0666; A61M 16/0825; A61M 16/0833; A61M 16/0841; A61M 16/0875; A61M 16/106; A61M 16/107; A61M 16/161; A61M 16/204; A61M 2016/0018; A61M 2016/0027; A61M 2016/0039; A61M 2016/0042; A61M 2205/3317; A61M 2205/3331; A61M 2205/3334; A61M 2205/3337; A61M 2205/3365; A61M 2205/3368; A61M 2205/3592; A61M 2205/50; A61M 2205/581; A61M 2205/70; A61M 2205/8206; A61M 2205/8237; A61M 2205/8275; A61M 2230/43; A61M 2230/46; A61M 16/0051; A61M 16/0009; A61M 2016/021; A61M 2016/0024; A61M 2016/0036; A61M 16/0069; A61M 2016/0015; A61M 2016/102–103; A61M 16/0018; A61M 16/0027; A61M 16/003; A61M 16/201–209; A61M 16/1005–1015; A61M 16/0015; A61M 16/0024; A61M 16/026; A61M 16/0033; A61M 16/0036; A61M 16/0039; A61M 16/0042; A61M 16/102–103; A61M 16/085; A61M 2230/40; A61M 2230/42; A61M 2230/432; A61M 2230/435; A61M 2230/437; A61M 2230/04; A61B 5/087–09
See application file for complete search history.

(56) References Cited

U.S. PATENT DOCUMENTS

| | | | |
|---|---|---|---|
| 8,360,061 | B2 | 1/2013 | Brown |
| 2002/0111571 | A1 | 8/2002 | Warwick |
| 2003/0192545 | A1 | 10/2003 | Truitt |
| 2005/0051174 | A1 | 3/2005 | Emerson |
| 2007/0186928 | A1 | 8/2007 | Be'eri |
| 2007/0199566 | A1 | 8/2007 | Be'eri |
| 2010/0122699 | A1 | 5/2010 | Birnkrant |
| 2013/0220324 | A1* | 8/2013 | Jafari ............... A61M 16/0006 128/204.23 |
| 2013/0220325 | A1 | 8/2013 | Davis |
| 2014/0150790 | A1* | 6/2014 | Meyer ............... A61M 16/0006 128/204.18 |
| 2016/0121062 | A1* | 5/2016 | Davenport ........ A61M 16/0006 601/47 |

FOREIGN PATENT DOCUMENTS

| | | | | |
|---|---|---|---|---|
| WO | WO2011010279 | A1 | 1/2011 | |
| WO | WO2011058470 | A1 | 5/2011 | |
| WO | WO2013118061 | A1 | 8/2013 | |
| WO | WO-2013182944 | A1 * | 12/2013 | ........ A61M 16/0009 |
| WO | WO2013182944 | A1 | 12/2013 | |
| WO | WO2016067147 | A1 | 5/2016 | |

OTHER PUBLICATIONS

Hogg, J. C. et al., "Pathophysiology of Airflow Limitation in Chronic Obstructive Pulmonary Disease." The Lancet, vol. 364, No. 9435, pp. 709-721, 2004.

Malik S.K. et al., "Alterations in Airway Dynamics Following Inhalation of Ultrasonic Mist." Chest, vol. 62, No. 6, pp. 660-664, Dec. 1972.

Kahn S.Y. et al., "Is Nebulized Saline a Placebo in COPD?", BMC Pulmonary Medicine, vol. 4, No. 9, pp. 1-5, 2004.

Yanai M. et al., "Deposition and Clearance of Inhaled 18FDG Powder in Patients with Chronic Obstructive Pulmonary Disease", European Respiratory Society, vol. 11, pp. 1342-1348, 1998.

\* cited by examiner

SECRETION LOOSENING AND COUGH SEGMENTING THERAPY

CROSS-REFERENCE TO RELATED APPLICATIONS

This patent application claims the priority benefit under 35 U.S.C. § 371 of international patent application no. PCT/IB2015/059655, filed Dec. 16, 2015, which claims the priority benefit under 35 U.S.C. § 35 U.S.C. § 365(b) and § 11 of International Application No. PCT/CN2014/095098, filed on Dec. 26, 2014, the contents of which are herein incorporated by reference.

BACKGROUND OF THE INVENTION

1. Field of the Invention

The present disclosure pertains to a method and system for providing loosening therapy to help loosen respiratory secretions and cough segmenting therapy to aid cough productivity in a subject.

2. Description of the Related Art

Systems that loosen airway secretions are known. The loosening of secretions within the airway is often achieved by shaking or vibrating the airway of a patient. Vibration of secretions tends to reduce their adhesion to the walls of the airway. Vibration of secretions is typically induced via pressure oscillations in the airway of the patient. Aiding the productivity of coughing for patients who have chronic high secretion production and/or reduced ability to generate significant cough flow due to lung dysfunction (e.g. COPD) is also known. Such cough assist devices typically use high amplitude pressure oscillations to aid movement of respiratory system secretions up and out airways of a patient. Secretion loosening devices and cough assist devices are separate devices used at separate times by the patient.

SUMMARY OF THE INVENTION

Accordingly, one or more aspects of the present disclosure relate to a system configured to provide loosening therapy and cough segmenting therapy to a subject. In some embodiments, the system comprises a subject interface, a segmenter, a loosener, one or more sensors, one or more physical computer processors, and/or other components. The subject interface is configured to communicate gas with an airway of the subject. The segmenter is configured to selectively control gas flow through the subject interface to provide high amplitude pressure oscillations during exhalation such that the high amplitude pressure oscillations aid cough productivity in the subject. The loosener is configured to selectively control gas flow through the subject interface to provide low amplitude pressure oscillations during inhalation and exhalation such that the low amplitude pressure oscillations loosen respiratory secretions. The one or more sensors are configured to generate output signals conveying information related to one or more gas parameters within the subject interface. The one or more physical computer processors are configured by computer-readable instructions to detect one or more trigger events based on the output signals such that the one or more trigger events include a loosening trigger event and a segmenting trigger event; responsive to detecting the loosening trigger event, control the loosener to provide the low amplitude pressure oscillations; and, responsive to detecting the segmenting trigger event, control the segmenter to provide the high amplitude pressure oscillations.

Yet another aspect of the present disclosure relates to a method for providing loosening therapy and cough segmenting therapy to a subject with a system. In some embodiments, the system comprises a subject interface, a segmenter, a loosener, one or more sensors, one or more physical computer processors, and/or other components. The method comprises communicating gas with an airway of the subject with the subject interface; controlling gas flow selectively through the subject interface with the segmenter to provide high amplitude pressure oscillations during exhalation such that the high amplitude pressure oscillations aid cough productivity in the subject; controlling gas flow selectively through the subject interface with the loosener to provide low amplitude pressure oscillations during inhalation and exhalation such that the low amplitude pressure oscillations loosen respiratory secretions; generating output signals conveying information related to one or more gas parameters within the subject interface with the one or more sensors; detecting one or more trigger events based on the output signals with the one or more physical computer processors, the one or more trigger events including a loosening trigger event and a segmenting trigger event; and controlling, with the one or more physical computer processors, the loosener to provide the low amplitude pressure oscillations responsive to detecting the loosening trigger event, and controlling, with the one or more physical computer processors, the segmenter to provide the high amplitude pressure oscillations responsive to detecting the segmenting trigger event.

Still another aspect of present disclosure relates to system for providing loosening therapy and cough segmenting therapy to a subject. In some embodiments, the system comprises means for communicating gas with an airway of the subject; means for selectively controlling gas flow through the means for communicating to provide high amplitude pressure oscillations during exhalation such that the high amplitude pressure oscillations aid cough productivity in the subject; means for selectively controlling gas flow through the means for communicating to provide low amplitude pressure oscillations during inhalation and exhalation such that the low amplitude pressure oscillations loosen respiratory secretions; means for generating output signals conveying information related to one or more gas parameters of the gas in the means for communicating; means for detecting one or more trigger events based on the output signals, the one or more trigger events including a loosening trigger event and a segmenting trigger event; and means for providing the low amplitude pressure oscillations responsive to detecting the loosening trigger event, and for providing the high amplitude pressure oscillations responsive to detecting the segmenting trigger event.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
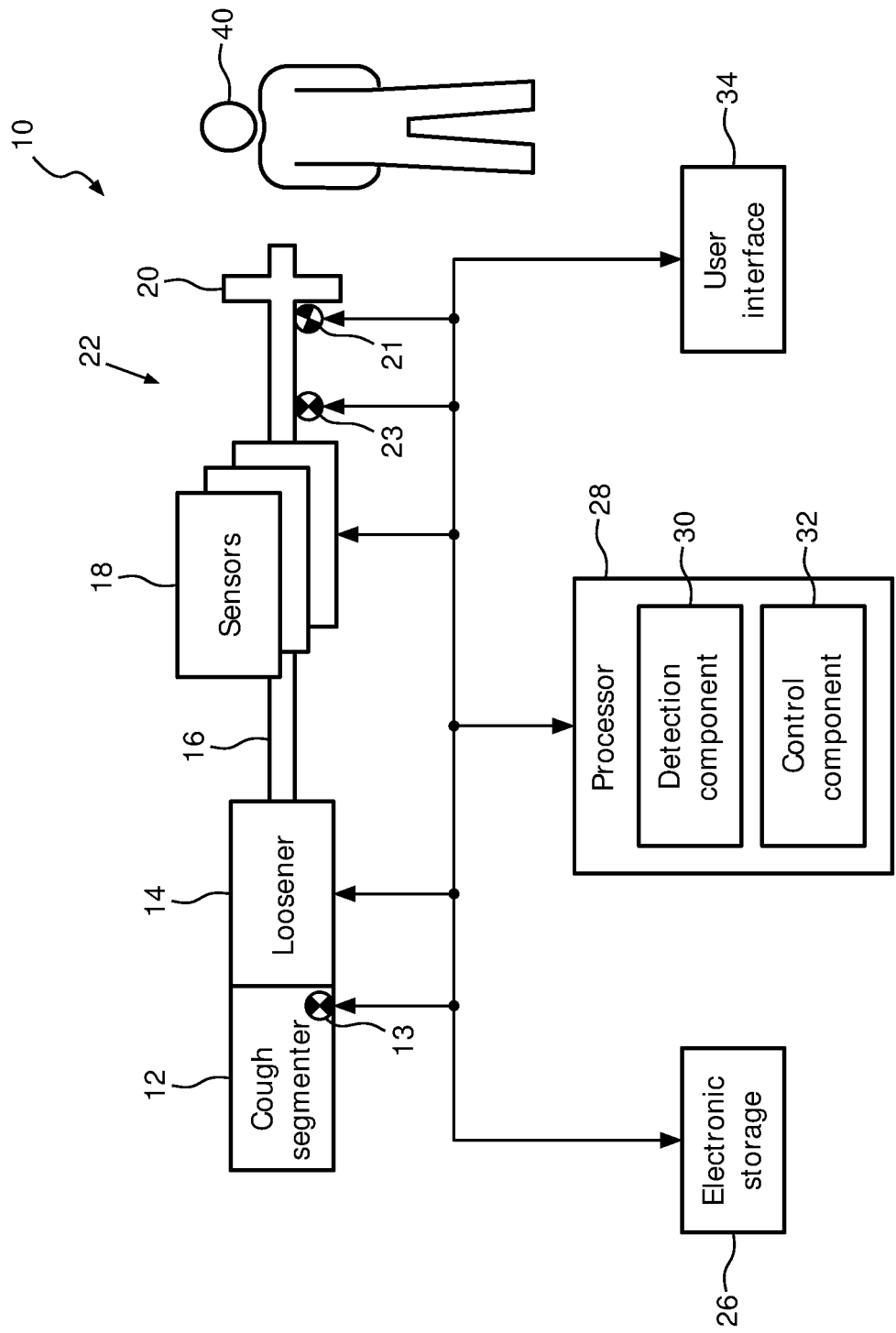
FIG. 1 is a schematic illustration of a system for providing loosening therapy and cough segmenting therapy a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates an exemplary embodiment of a system 10 configured to provide loosening therapy and cough segmenting therapy to a subject 40. System 10 combines a loosener ("secretion loosener" to loosen respiratory secretions) and a segmenter ("cough segmenter" to aid cough productivity) into one compact and efficient device. System 10 may be used as a combinational loosening and cough segmentation system to aid the movement and expulsion of airway secretions, as a loosening device only, as a segmenting device only, and/or as a diagnostic data collection system. System 10 may enable relatively low amplitude pressure oscillations to be generated by a patient's inspiratory and expiratory flow while breathing to loosen respiratory secretions and aid cough productivity. System 10 may be a stand-alone device, and/or part of a larger respiratory therapy system. Airflow in system 10 is produced by the patient. (This is not intended to be limiting. Outside gas sources may be used with system 10 and may produce some and/or all of the airflow in system 10.) System 10 may be used to produce high amplitude pressure oscillations during an exhalation manoeuver (via the segmenter), and lower pressure oscillations during the full breathing cycle (via the loosener) of the subject. In some embodiments system 10 comprises one or more of a subject interface 22, a segmenter 12, a loosener 14, one or more sensors 18, one or more physical computer processors 22, a user interface 24, an electronic storage 26, and/or other components.

Subject interface 22 is configured to communicate breathable gas to and/or from an airway of subject 40. As such, subject interface 22 comprises a conduit 16, an interface appliance 20, and/or other components. In some embodiments, conduit 16 is configured to convey the flow of gas to and/or from interface appliance 20. Interface appliance 20 is configured to deliver the flow of gas to the airway of subject 40 and/or otherwise communicate with the airway of subject 40. In some embodiments, interface appliance 20 is configured to be non-invasively engaged by subject 40. Non-invasive engagement comprises removably engaging one or more external orifices of the airway of subject 40 (e.g., nostrils and/or mouth) to communicate gas between the airway of subject 40 and interface appliance 20. In some embodiments, interface appliance 20 is removably coupled to conduit 16. Interface appliance 20 may be removed for cleaning and/or for other purposes.

In some embodiments, conduit 16 is configured as a mouthpiece to be engaged by the mouth of subject 40. In some embodiments, other non-invasive interface appliances may be configured as interface appliance 20. Some examples of non-invasive interface appliance 20 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance. In some embodiments, system 10 may be connected to a classical respiratory circuit (e.g., a six foot hose) such that the classical respiratory circuit functions as subject interface 22.

Segmenter 12 is configured to selectively control gas flow through subject interface 22. In some embodiments, segmenter 12 is configured to control gas flow to provide high amplitude pressure oscillations during exhalation such that the high amplitude pressure oscillations aid cough productivity in subject 40. In some embodiments, segmenter 12 may be controlled and/or powered by exhalation of subject 40, cough effort of subject 40, one or more processors 28, manually by subject 40 and/or other users, and/or other mechanisms. In some embodiments, segmenter 12 may comprise one or more valves (in series and/or parallel), control knobs/buttons (e.g. manually set how far a valve can open), a housing, wiring and/or other components communicating with processor 28, a flow path and components configured to couple the flow path with the subject interface 20, and/or other components.

In some embodiments, segmenter 12 may be and/or include a valve 13. Valve 13 may be configured to alternatively block the flow of gas and release the flow of gas several times during a cough and/or an exhalation. Blocking and releasing the flow of gas may produce several high pressure flow peaks during an exhalation phase which may increase the efficiency of the coughing effort. In some embodiments, valve 13 may be an oscillating valve having a relatively high flow resistance when closed and a lower resistance when open. In some embodiments, valve 13 may be a rotating valve, a sleeve valve, and/or any other type of valve that oscillates between an open and closed position. In some embodiments, segmenter 12 may provide oscillating flows between about 100 and about 300 Liters/Minute (LPM) peak to peak, at a frequency between about 2 Hz and about 10 Hz.

Figure 2:
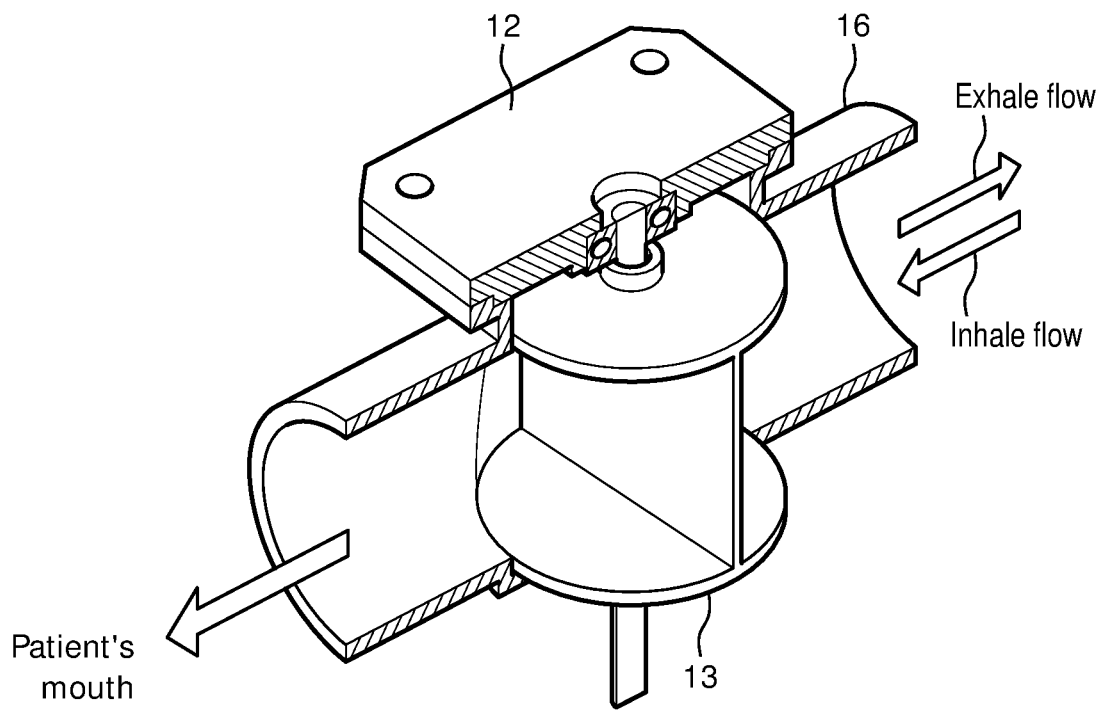
FIG. 2 illustrates an example of a segmenter.

By way of non-limiting example, FIG. 2 illustrates an example of segmenter 12. As shown in FIG. 2, segmenter 12 includes valve 13. In the example shown in FIG. 2, valve 13 is a rotary 27 valve which causes pressure oscillations by blocking and/or permitting gas flow to and/or from subject 40 through conduit 16. Valve 13 may produce high amplitude pressure to aid expulsion of secretions, for example.

Referring back to FIG. 1, loosener 14 is configured to selectively control gas flow through subject interface 22. In some embodiments, loosener 14 is configured to provide low amplitude pressure oscillations during inhalation and exhalation such that the low amplitude pressure oscillations loosen respiratory secretions in subject 40. In some embodiments, loosener 14 may be controlled and/or powered by a subject's (e.g., subject 40) inspiratory and expiratory flow while breathing, one or more processors 28, manually by a user, and/or other mechanisms. In some embodiments, loosener 14 may comprise one or more valves (in series and/or parallel), control knobs/buttons (e.g. manually set how far a valve can open), a housing, wiring and/or other components communicating with processor 28, a flow path and components configured to couple the flow path with the subject interface 20, and/or other components.

In some embodiments, loosener 14 may comprise a variable resistance (e.g. a valve) such that, when subject 40 breaths, low amplitude pressure oscillations are produced in the airways of subject 40. The low pressure oscillations may cause loosening of secretions in lungs. Loosener 14 may be configured to alternatively block the flow of gas and release the flow of gas several times during normal breathing (e.g., during an inhalation and/or an exhalation). In some embodiments, loosener 14 may provide pressure oscillations between about −3 cm $H_2O$ and about 7 cm $H_2O$, at a frequency between about 5 Hz and about 20 Hz, which may cause oscillating flows between about 10 and about 40 Liters/Minute (LPM) peak to peak.

Figure 3:
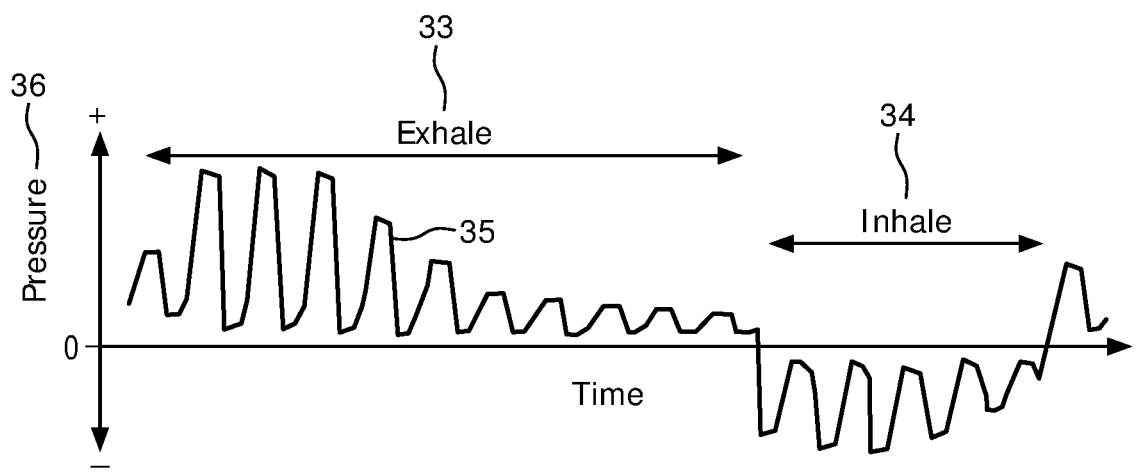
FIG. 3 illustrates an example of pressure oscillations of a loosener.

FIG. 3 shows an example of pressure 36 oscillations 35 during exhalation 33 and inhalation 34, caused by loosener 14 (FIG. 1). In the example shown in FIG. 3, oscillations 35 are generated during a subject's inhalation 34 and exhalation 33 when the flow of gas passing through loosener 14 is alternatively blocked and released (as described above).

In some embodiments, loosener 14 may be and/or include a shunt valve 23. Shunt valve 23 is configured to control whether system 10 provides low amplitude pressure oscillations or high amplitude pressure oscillations. In some embodiments, shunt valve 23 may be configured such that when open, system 10 provides low amplitude pressure oscillations, and when closed, system 10 provides high amplitude pressure oscillations. For example, when shunt valve 23 is open, gas that would otherwise flow through segmenter 12 and be segmented into high amplitude pressure oscillations is diverted through shunt valve 23. This effectively dampens the oscillations received by subject 40.

In some embodiments, shunt valve 23 may be located and/or included in segmenter 12, loosener 14, subject interface 22, interface appliance 20, and/or any location within system 10.

In some embodiments, shunt valve 23 may be of fixed resistance, variable resistance with closed loop control (e.g., via processor 28), and/or include other types of valves. In some embodiments, shunt valve 23 may be a controllable valve. For example, shunt valve 23 may be a simple open/close valve that is manually controlled by the subject. In some embodiments, shunt valve 23 may include an electro-mechanical actuator such as a solenoid energized by a switch and/or an electronic micro-controller such as processor(s) 28. In some embodiments, the actuation of shunt valve 23 may permit various flow resistances to be selected. For example, shunt flow may be a flow port with a fixed resistance, but the resistance may be manually adjustable for a therapy session by affixing inserts or attachments that have various port opening sizes.

Figure 4:
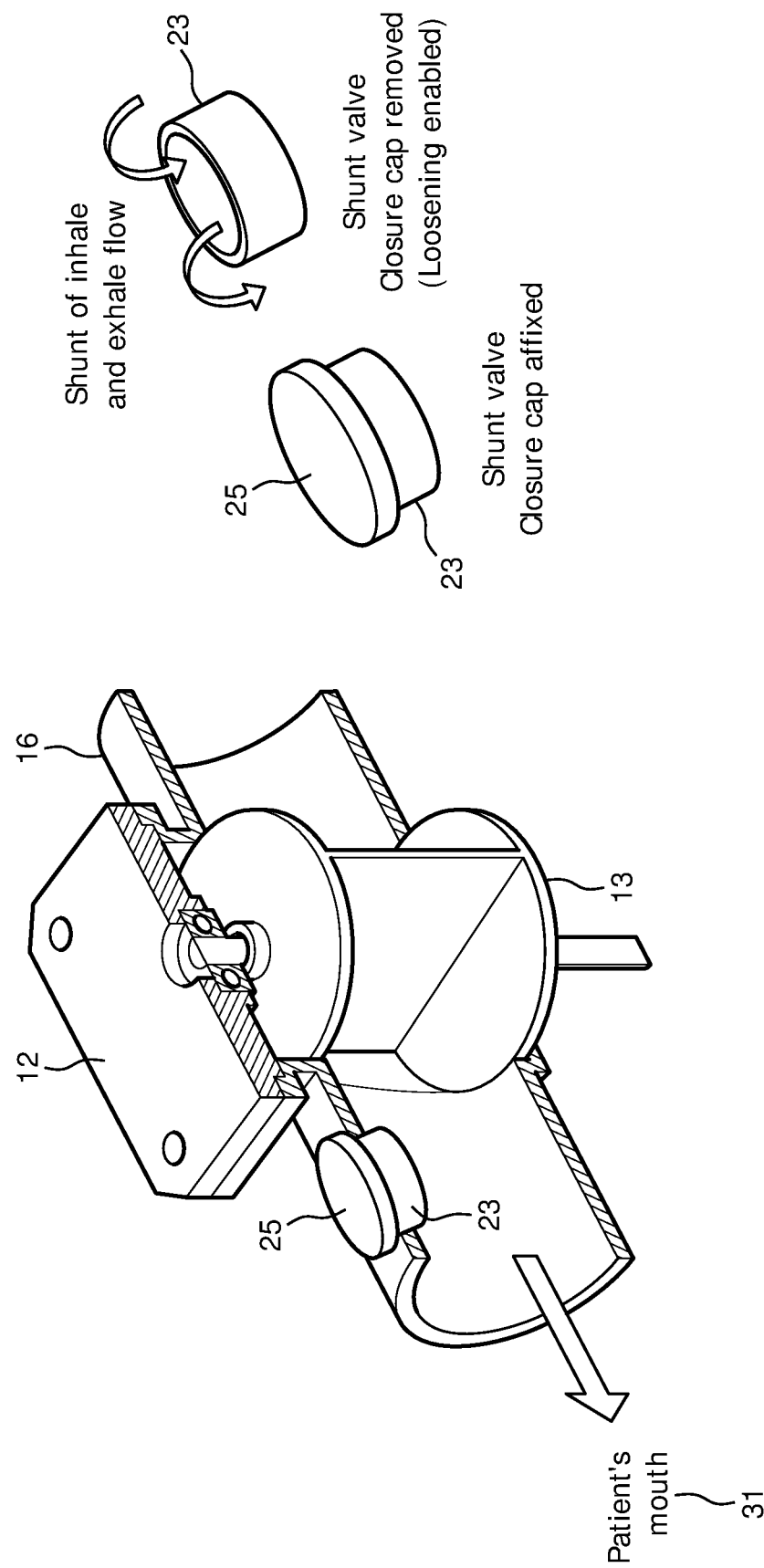
FIG. 4 illustrates an example of a shunt valve.

FIG. 4 shows an example of shunt valve 23 within system 10. In this example, shunt valve 23 is a shunt flow port which uses a manually affixed or removed closure cap 25 to block flow or permit flow to and/or from subject 40. In some embodiments, shunt valve 23 is located on a subject side 31 of segmenter 12. Closure cap 25 may be a screw-on lid, snap-on lid, a sliding door, and/or other closure cap that opens and closes the port. This description of shunt valve 23 is not intended to be limiting. As described herein, shunt valve 23 may also be electrically actuated by a solenoid and/or a motor, for example, that opens and/or closes shunt valve 23 as described herein.

In some embodiments, shunt valve 23 may be dynamically controlled by one or more processors 28, and/or other mechanisms. For example, shunt valve 23 may be controlled to cause various air flow resistances of different amounts based on one or more of output signals from sensors 18, information (e.g., gas parameters, breathing parameters, etc.) determined by processors 28, user input, and/or other information.

In some embodiments, loosener 14 includes a pressure generator configured to generate a bias pressure such that the loosening is performed with the bias pressure and the low amplitude pressure oscillations. In some embodiments the pressure generator may be configured to provide CPAP, BiPAP, and/or other pressure regimes. In some embodiments, the low amplitude pressure oscillations center on the bias pressure (e.g. 4-20 cmH2O) provided by the pressure generator, to make it easier for subject 40 to breath (e.g. subjects with COPD).

Sensors 18 are configured to generate output signals conveying information related to one or more gas parameters of the gas within subject interface 22. The one or more gas parameters may comprise gas parameters related to the flow of gas, breathing parameters related to respiration of subject 40, oscillation parameters, physiological parameters of subject 40, and/or other parameters. The one or more gas parameters of the flow of gas may comprise, for example, one or more of a flow rate, a volume, a pressure, humidity, temperature, acceleration, velocity, and/or other gas parameters. Breathing parameters related to the respiration of subject 40 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters. Oscillation parameters may comprise an oscillation frequency, an oscillation amplitude, and/or other parameters. Physiological parameters may include oximetry parameters, a pulse, a heart rate, a temperature, a blood pressure, and/or other physiological parameters.

Sensors 18 may comprise one or more sensors that measure such parameters directly (e.g., through fluid communication with the flow of gas in subject interface 22). Sensors 18 may comprise one or more sensors that generate output signals related to one or more parameters of the flow of gas indirectly. Although sensors 18 are illustrated at a single location within (or in communication with) conduit 16 between loosener 14 and interface appliance 20, this is not intended to be limiting in any way. Sensors 18 may include sensors disposed in a plurality of locations, such as, for example, within loosener 14, within segmenter 12, within (or in communication with) interface appliance 20, coupled with and/or within subject interface 22, and/or other locations of system 10.

Processor 28 is configured to provide information processing capabilities in system 10. As such, processor 28 includes one or more of a digital processor, an analog processor, a digital circuit designed to process information, an analog circuit designed to process information, a state machine, and/or other mechanisms for electronically processing information. Although processor 28 is shown in FIG. 1 as a single entity, this is for illustrative purposes only. In some implementations, processor 28 includes a plurality of processing units. These processing units may be physically located within the same device, or processor 28 may represent processing functionality of a plurality of devices operating in coordination.

As shown in FIG. 1, processor 28 is configured to execute one or more computer program components. The one or more computer program components may comprise one or more of a detection component 30, a control component 32, and/or other components. Processor 28 may be configured to execute components 30 and 32 by software; hardware; firmware; some combination of software, hardware, and/or firmware; and/or other mechanisms for configuring processing capabilities on processor 28.

It should be appreciated that although components 30 and 32 are illustrated in FIG. 1 as being co-located within a single processing unit, in implementations in which processor 28 comprises multiple processing units, one or more of components 30 and/or 32 may be located remotely from the other components. The description of the functionality provided by the different components 30 and/or 32 described below is for illustrative purposes, and is not intended to be limiting, as any of components 30 and/or 32 may provide more or less functionality than is described. For example, one or more of components 30 and/or 32 may be eliminated, and some or all of its functionality may be provided by other components 30 and/or 32. As another example, processor 28 may be configured to execute one or more additional components that may perform some or all of the functionality attributed below to one of components 30 and/or 32.

Detection component 30 is configured to detect one or more trigger events. In some embodiments, the one or more trigger events may include a loosening trigger event, a segmenting trigger event, and/or other triggering events. In some embodiments, the one or more trigger events may be detected responsive to receiving an indication of a manual action performed by a user. In some embodiments, the one or more trigger events may be detected based on the output signals from sensors 18, parameters determined by detection component 30 (described below), obtained threshold information (described below), and/or other information.

In some embodiments, detection component 30 may be configured to determine one or more parameters in system 10. The one or more parameters may include gas parameters, breathing parameters, physiological parameters, and/or other parameters. The gas parameters may include parameters of the gas flow through subject interface 22 and/or other parameters. In some embodiments, determining parameters of the gas flow and/or the other parameters may be based on the output signals, and/or other information. In some embodiments, the parameters of the gas flow may include one or more loosening parameters, one or more segmenting parameters, and/or other parameters. In some embodiments, the loosening and/or segmenting parameters may include pressure parameters, flow parameters, breathing parameters, physiological parameters, and/or other parameters.

In some embodiments detection component 30 may be configured to obtain threshold values for the one or more loosening parameters and the one or more segmenting parameters. In some embodiments, threshold values may be configurable by subject 40, predefined at manufacture, determined based on previous respiration by subject 40, determined based on the gas parameters within system 10, and/or determined in other manners. In some embodiments, the threshold values may be provided and/or may be changed by subject 40 using user interface 24, for example.

In some embodiments detection component 30 may be configured to compare the one or more loosening parameters to the threshold values for the one or more loosening parameters, and to compare the one or more segmenting parameters to the threshold values for the one or more segmenting parameters. In some embodiments, detection component 30 may be configured to, responsive to an individual loosening parameter breaching a corresponding threshold value for the individual loosening parameter, detect the loosening trigger event. In some embodiments, responsive to an individual segmenting parameter breaching a corresponding threshold value for the individual segmenting parameter, detect the segmenting trigger event such that the segmenting trigger event is independently detected.

Control component 32 is configured to, responsive to detection component 30 detecting a loosening trigger event, control loosener 14 to provide the low amplitude pressure oscillations. In some embodiments control component 32 is configured to, responsive to detecting the segmenting trigger event, control segmenter 12 to provide the high amplitude pressure oscillations. Control component 32 is configured to control loosener 14 and segmenter 12 based on the output signals, parameters determined by detection component 30, information entered and/or received via user interface 24, information stored in electronic storage 26 and/or other information.

Figure 5:
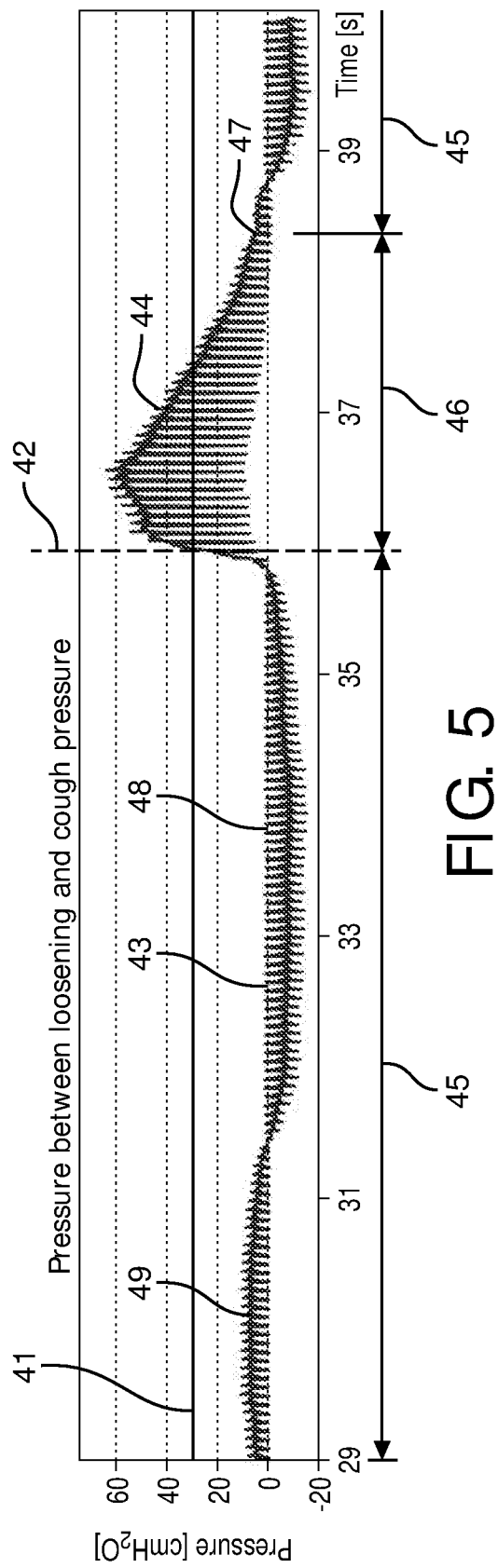
FIG. 5 illustrates a first example of loosening and/or segmenting thresholds.

By way of non-limiting example, FIG. 5 shows an example of pressure oscillations 43 during loosening 45 and segmenting 46. In this example, system 10 (FIG. 1) starts in a loosening mode 45 during inhalation 48 and exhalation 49, with loosening pressure oscillations 43 having low amplitudes. When the pressure during exhalation 49 reaches a threshold pressure 41, system 10 automatically switches to the cough segmentation mode 46 with segmenting pressure oscillations 44 having high a amplitude. Instant 42 shows the moment of switching from loosening 45 to segmentation 46. As shown in FIG. 5, after a loosening threshold 47 is reached, system 10 switches back from cough segmentation 46 to loosening 45. System 10 is the ready to detect the next cough and switch back to cough segmentation 46 if threshold 41 again reached.

Figure 6:
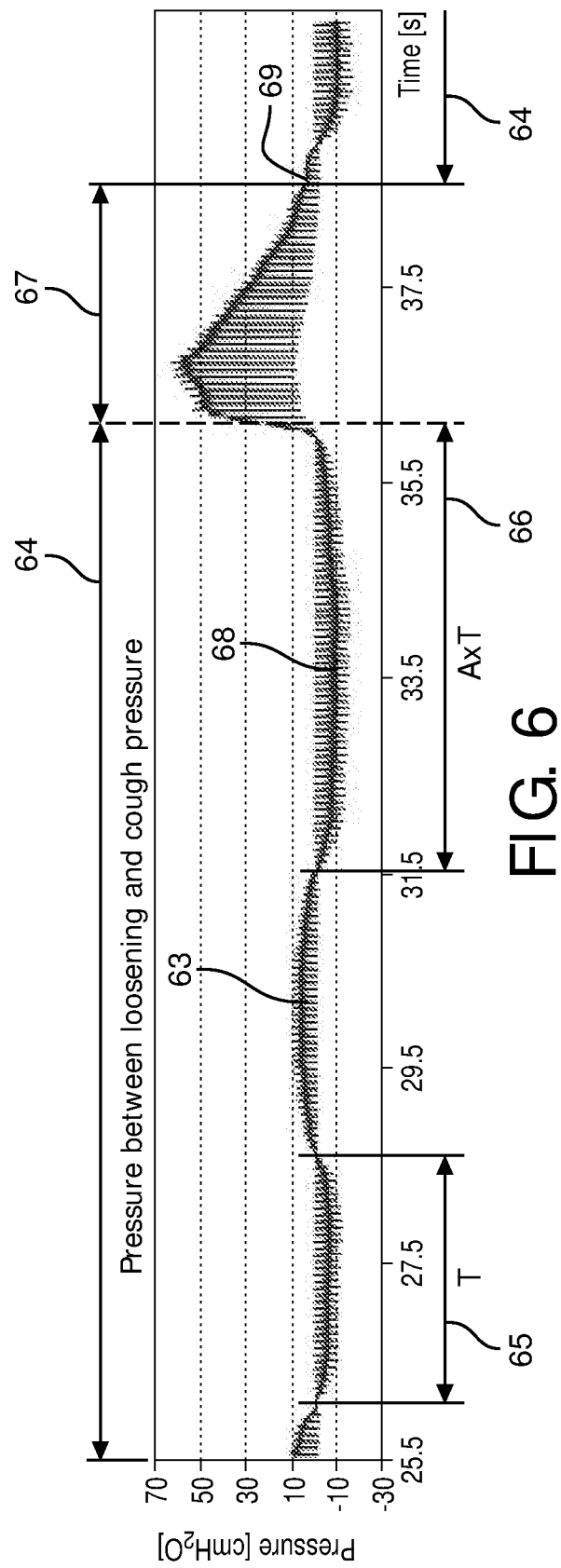
FIG. 6 illustrates a second example of loosening and/or segmenting thresholds.

FIG. 6 illustrates an example of pressure oscillations 63 during loosening 64 and segmenting 67 where loosening and/or segmenting trigger events are detected based on breathing parameters of the subject. In FIG. 6, a segmenting trigger event 66 is detected during a period of negative pressure during inhalation 68 (e.g., detecting a deep inhalation preceding a cough). In this example, system 10 (FIG. 1) starts in a loosening mode 64 during several inhalations and exhalations, with loosening pressure oscillations 63 having low amplitudes. During the loosening mode 64 an average duration 65 of inhalation (e.g., one of possible parameters determined by detection module 30 shown in FIG. 1) is determined during multiple breaths. Based on the average duration of inhalation, a duration threshold 66 is determined (e.g., by detection module 30). When threshold duration 66 for duration of a negative pressure has been breached, system 10 automatically switches to cough segmentation mode 67. After a loosening threshold 69 is reached, system 10 switches back from cough segmentation mode 67 to loosening mode 64. Once back in loosening mode 64, system 10 is ready to detect the next cough and switch back to cough segmentation mode 67 if the threshold duration 66 has been reached.

Referring back to FIG. 1, in some embodiments, system 10 comprises a pressure relief valve 21. In some embodiments, pressure relief valve 21 is coupled with subject interface 22 and configured to open and release gas out of subject interface 22 responsive to pressure within subject interface 22 exceeding a predetermined pressure relief threshold value so as to maintain the pressure within subject interface 22 within a desired range during the high amplitude pressure oscillations and/or the low amplitude pressure oscillations. In some embodiments, the predetermined pressure relief threshold value may be up to about 21 cm $H_2O$. In some embodiments, the predetermined pressure relief threshold value may be up to about 40 cm $H_2O$.

In some embodiments, the predetermined pressure relief threshold value may be up to about 60 cm $H_2O$. In some embodiments, the predetermined pressure relief threshold value may be between about 20 and about 100 cm $H_2O$. In some embodiments, the predetermined pressure relief threshold range may be between about 20 and about 60 cm $H_2O$. In some embodiments, pressure relief valve 21 may be controlled manually, by processors 28, and/or other mechanisms. In some embodiments, shunt valve 23 may be pressure relief valve 21. For example, in such embodiments, shunt valve 23 may be controlled to open when the pressure in subject interface 22 exceeds a positive and/or negative pressure relief threshold (e.g. +/−40 cm $H_2O$).

The predetermined pressure relief threshold values are stored in a memory of system 10 (e.g., electronic storage 26) and/or in other locations. The predetermined pressure relief threshold values may be configurable by subject 40 and/or other users, predefined at manufacture, determined dynamically based on previous respiration by subject 40, determined dynamically based on the output signals, and/or determined in other manners. The predetermined pressure relief threshold values may be provided and/or may be changed by subject 40 using user interface 24, for example. In some embodiments, when pressure relief valve 21 is configured to operate mechanically (e.g., pressure relief valve 21 is not controlled by processor 28 based on output signals from sensors 18 to operate), the predetermined pressure relief threshold values may be set by a manufacturer, by subject 40 and/or other users through mechanical adjustment of pressure relief valve 21.

In some implementations, pressure relief valve 21 may be located at one or more locations within system 10. For example, in some embodiments, pressure relief valve 21 may be located in and/or on subject interface 22 as shown in FIG. 1. It should be appreciated that pressure relief valve 21 may be located elsewhere within subject interface 22 and/or other components of system 10 so long as pressure relief valve 21 is in communication with the gas flowing through subject interface 22.

Referring back to FIG. 1, user interface 24 is configured to provide an interface between system 10 and subject 40 and/or other users through which subject 40 and/or other users may provide information to and receive information from system 10. Other users may comprise, for example, a caregiver, a doctor, and/or other users. This enables data, cues, results, and/or instructions and any other communicable items, collectively referred to as "information," to be communicated between a user (e.g., subject 40), processor 28, and/or other components of system 10. Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 24 comprises a plurality of separate interfaces.

It is to be understood that other communication techniques, either hard-wired or wireless, are also contemplated by the present disclosure as user interface 24. For example, the present disclosure contemplates that user interface 24 may be integrated with a removable storage interface provided by electronic storage 26. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

In some embodiments, electronic storage 26 comprises electronic storage media that electronically stores information. The electronic storage media of electronic storage 26 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 26 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 26 may store software algorithms, information determined by processor 28, information received via user interface 24, and/or other information that enables system 10 to function properly. Electronic storage 26 may be (in whole or in part) a separate component within system 10, or electronic storage 26 may be provided (in whole or in part) integrally with one or more other components of system 10 (e.g., user interface 24, processor 28, etc.).

Information determined by processor 28 and/or stored by electronic storage 26 may comprise information related to respiration of subject 40, compliance, use frequency, and/or other information. The information stored by electronic storage 26 may be viewed via user interface 24, by connecting (wired and/or wireless) to a separate computer, and/or other via other methods. The information stored by electronic storage 26 may be used, for example, to adjust therapy settings, used by a doctor to make medical decisions, and/or for other uses. In some embodiments, system 10 may include a wireless transmitter (not shown) and the information determined by processor 28, the information stored by electronic storage 26, and/or other information may be communicated to a care giver, for example, over a wireless network. By way of a non-limiting example, the care giver may receive use information, patient status, and/or other information, allowing the care giver to remotely track the therapy delivered by system 10.

Figure 7:
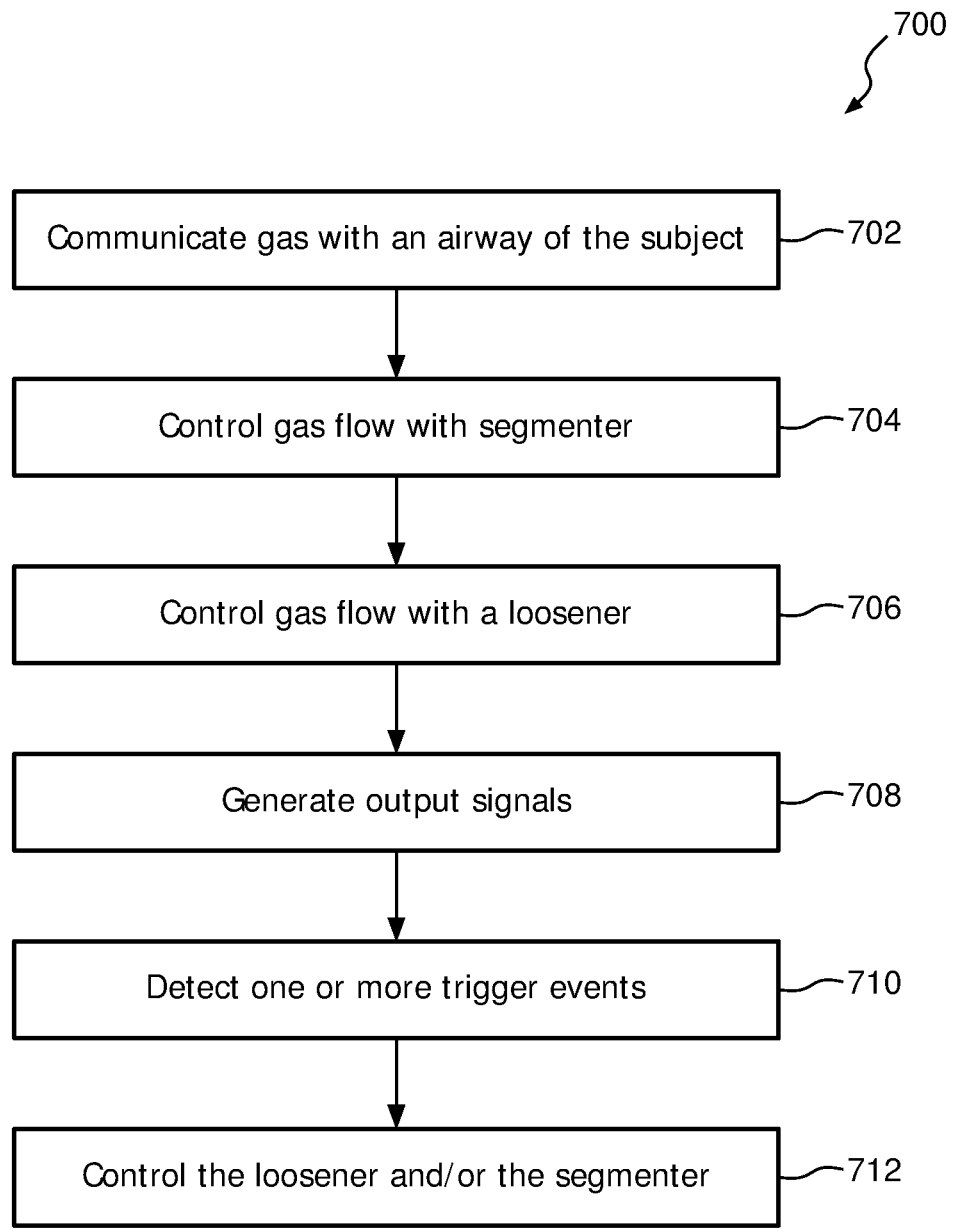
FIG. 7 illustrates a method for providing variable amplitude pressure oscillations.

FIG. 7 illustrates a method 700 for providing loosening therapy and cough segmenting therapy to a subject with a system. The system may comprise a subject interface, a segmenter, a loosener, one or more sensors, one or more physical computer processors, and/or other components. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, gas is communicated with an airway of the subject. In some embodiments, the gas is communicated with an airway of the subject by a subject interface similar to and/or the same as subject interface 22 (shown in FIG. 1 and described herein).

At an operation 704, gas flow is selectively controlled through the subject interface. In some embodiments gas flow is selectively controlled with a segmenter similar to and/or the same as segmenter 12 (shown in FIG. 1 and described herein). In some embodiments, the gas flow is selectively controlled to provide high amplitude pressure oscillations during exhalations such that the high amplitude oscillations aid cough productivity in the subject.

At an operation 706, gas flow is selectively controlled through the subject interface. In some embodiments gas flow is selectively controlled with a loosener similar to and/or the same as loosener 14 (shown in FIG. 1 and described herein). In some embodiments, the gas flow is selectively controlled to provide low amplitude pressure oscillations during inhalation and exhalation such that the low amplitude pressure oscillations loosen respiratory secretions in the subject.

In some embodiments, loosener 14 includes a pressure generator configured to generate a bias pressure such that the loosening is performed with the bias pressure and the low amplitude pressure oscillations. In some embodiments the pressure generator may be configured to provide CPAP, BiPAP, and/or other pressure regimes.

At operation 708, output signals conveying information related to one or more gas parameters of the gas within the subject interface are generated. In some embodiments the output signals are generated by one or more sensors similar to and/or the same as to sensors 18 (shown in FIG. 1 and described herein).

At operation 710, one or more trigger events are detected based on the output signals. In some embodiments, the one or more trigger events are detected by one or more physical computer processors similar to and/or the same as one or more physical computer processors 28 (shown in FIG. 1 and described herein). In some embodiments, the one or more trigger events include a loosening trigger event and/or a segmenting trigger event.

In some embodiments, the one or more trigger events are detected responsive to the one or more physical computer processors receiving an indication of a manual action performed by the use. In some embodiments, operation 710 includes determining parameters of the gas flow through the subject interface. In some embodiments, determining parameters of the gas flow through the subject interface may be based on the output signals. Parameters of the gas flow through the subject interface may include one or more loosening parameters, one or more segmenting parameters, and/or other parameters. In some embodiments operation 710 includes obtaining threshold values for the one or more loosening parameters and the one or more segmenting parameters. In some embodiments, operation 710 includes comparing the one or more loosening parameters to the threshold values for the one or more loosening parameters, and/or comparing the one or more segmenting parameters to the threshold values for the one or more segmenting parameters. In some embodiments, operation 710 includes detecting the loosening trigger event responsive to an individual loosening parameter breaching a corresponding threshold value for the individual loosening parameter. In some embodiments, operation 710 includes detecting the segmenting trigger event responsive to an individual segmenting parameter breaching a corresponding threshold value for the individual segmenting parameter.

At operation 712, low amplitude pressure oscillations are provided responsive to detecting the loosening trigger event, and high amplitude pressure oscillations are provided responsive to detecting the segmenting trigger event. In some embodiments, providing low amplitude pressure oscillations and high amplitude pressure oscillations is controlled by one or more physical computer processors similar to and/or the same as one or more physical computer processors 28 (shown in FIG. 1 and described herein).

In some embodiments, the system may comprise a shunt valve. Operation 712 may further comprise controlling whether the shunt valve is open or closed, providing the low amplitude pressure oscillations when the shunt valve is open, and providing high amplitude pressure oscillations when the shunt valve is closed. In some embodiments, the system may comprise a pressure relief valve. Operation 712 may further comprise opening the pressure relief valve and releasing gas out of the subject interface. Opening the pressure relief valve and releasing gas out of the subject interface may be responsive to pressure within the subject interface exceeding a predetermined threshold value so as to maintain the pressure within the subject interface within a desired range during the high amplitude pressure oscillations and/or the low amplitude pressure oscillations.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to provide loosening therapy and cough segmenting therapy to a subject, the system comprising:
   a subject interface configured to communicate gas with an airway of the subject;
   a cough segmenter configured to selectively control gas flow through the subject interface to provide high amplitude pressure oscillations during exhalation such that the high amplitude pressure oscillations aid cough productivity in the subject;
   a secretion loosener configured to selectively control gas flow through the subject interface to provide low amplitude pressure oscillations during inhalation and exhalation such that the low amplitude pressure oscillations loosen respiratory secretions;
   one or more sensors configured to generate output signals conveying information related to one or more breathing parameters within the subject interface, wherein the one or more breathing parameters comprises one or more of a tidal volume, a timing of a beginning of inhalation, a timing of an end of inhalation, a timing of a beginning of exhalation, a timing of an end of exhalation, a respiration rate, a duration of inhalation, a duration of exhalation, a duration of a single breathing cycle, or a respiration frequency; and
   one or more physical computer processors, configured by computer-readable instructions to:
      detect two or more trigger events based on the output signals, the two or more trigger events including a loosening trigger event and a segmenting trigger event, wherein the loosening trigger event and the segmenting trigger event are independently detected; and
      responsive to detecting the loosening trigger event, switch the system to a secretion loosening mode and control the secretion loosener to provide the low amplitude pressure oscillations, and, responsive to detecting the segmenting trigger event, switch the system from the secretion loosening mode to a cough segmentation mode and control the cough segmenter to provide the high amplitude pressure oscillations.

2. The system of claim 1, wherein the two or more physical computer processors are configured such that detecting the two or more trigger events comprises:
   determining parameters of the gas flow through the subject interface based on the output signals, the parameters including one or more loosening parameters and one or more segmenting parameters;
   obtaining threshold values for the one or more loosening parameters and the one or more segmenting parameters;
   comparing the one or more loosening parameters to the threshold values for the one or more loosening parameters,
   comparing the one or more segmenting parameters to the threshold values for the one or more segmenting parameters;
   responsive to an individual loosening parameter breaching a corresponding threshold value for the individual loosening parameter, detecting the loosening trigger event; and
   responsive to an individual segmenting parameter breaching a corresponding threshold value for the individual segmenting parameter, detecting the segmenting trigger event.

3. The system of claim 1, wherein the one or more physical computer processors are configured such that the two or more trigger events is detected responsive to receiving an indication of a manual action performed by the user.

4. The system of claim 1, wherein loosener comprises a shunt valve configured to control whether the system provides low amplitude pressure oscillations or high amplitude pressure oscillations such that when the shunt valve is open, the system provides low amplitude pressure oscillations, and when the shunt valve is closed, the system provides high amplitude pressure oscillations.

5. The system of claim 1, wherein the cough segmenter comprises a rotary valve configured to block and/or permit gas flow to provide the high amplitude pressure oscillations.

6. The system of claim 1, wherein the secretion loosener includes a pressure generator configured to generate a bias pressure such that the loosening is performed with the bias pressure and the low amplitude pressure oscillations.

7. The system of claim 1, wherein the high amplitude pressure oscillations are selected to produce flows between about 100 lpm and about 300 lpm.

8. The system of claim 1, wherein the low amplitude pressure oscillations are selected to produce flows between about 10 lpm and about 40 lpm.

9. A method of operation of a system, the system comprising a subject interface, a cough segmenter, a secretion loosener, one or more sensors, and one or more physical computer processors, the method comprising:
   communicating gas with the subject interface;
   controlling gas flow selectively through the subject interface with the cough segmenter to provide high amplitude pressure oscillations during exhalation such that the high amplitude pressure oscillations aid cough productivity;
   controlling gas flow selectively through the subject interface with the secretion loosener to provide low amplitude pressure oscillations during inhalations and exhalations such that the low amplitude pressure oscillations loosen respiratory secretions;
   generating output signals conveying information related to one or more breathing parameters within the subject interface with the one or more sensors;
   detecting two or more trigger events based on the output signals with the one or more physical computer processors, the two or more trigger events including a loosening trigger event and a segmenting trigger event, wherein the loosening trigger event and the segmenting trigger event are independently detected; and
   controlling, with the one or more physical computer processors, the system to switch into a secretion loosening mode and to control the secretion loosener to provide the low amplitude pressure oscillations responsive to detecting the loosening trigger event, and controlling, with the one or more physical computer processors, the system to switch from the secretion loosening mode into a cough segmenting mode and control the cough segmenter to provide the high amplitude pressure oscillations responsive to detecting the segmenting trigger event.

10. The method of claim 9, wherein detecting the two or more trigger events comprises:
determining parameters of the gas flow through the subject interface based on the output signals, the parameters including one or more loosening parameters and one or more segmenting parameters;
obtaining threshold values for the one or more loosening parameters and the one or more segmenting parameters;
comparing the one or more loosening parameters to the threshold values for the one or more loosening parameters,
comparing the one or more segmenting parameters to the threshold values for the one or more segmenting parameters;
responsive to an individual loosening parameter breaching a corresponding threshold value for the individual loosening parameter, detecting the loosening trigger event; and
responsive to an individual segmenting parameter breaching a corresponding threshold value for the individual segmenting parameter, detecting the segmenting trigger event.

11. The method of claim 9, wherein detection of the two or more trigger events is responsive to receiving an indication of a manual action performed by the user.

12. The method of claim 9, wherein the secretion loosener comprises a shunt valve and the method further comprises providing low amplitude pressure oscillations when the shunt valve is open and providing high amplitude pressure oscillations when the shunt valve is closed.

13. The method of claim 9, wherein the cough segmenter comprises a rotary valve configured to block and/or permit gas flow to provide the high amplitude pressure oscillations.

14. The method of claim 9, wherein the secretion loosener includes a pressure generator configured to generate a bias pressure such that the loosening is performed with the bias pressure and the low amplitude pressure oscillations.

15. A system for providing loosening therapy and cough segmenting therapy to a subject, the system comprising:
means for communicating gas with an airway of the subject;
means for selectively controlling gas flow through the means for communicating to provide high amplitude pressure oscillations during exhalation such that the high amplitude pressure oscillations aid cough productivity in the subject;
means for selectively controlling gas flow through the means for communicating to provide low amplitude pressure oscillations during inhalation and exhalation such that the low amplitude pressure oscillations loosen respiratory secretions;
means for generating output signals conveying information related to one or more breathing parameters of the gas in the means for communicating;
means for detecting two or more trigger events based on the output signals, the two or more trigger events including a loosening trigger event and a segmenting trigger event, wherein the loosening trigger event and the segmenting trigger event are independently detected; and
means for controlling the means for selectively switching the system to a secretion loosening mode and from the secretion loosening mode to a cough segmenting mode by controlling gas flow through the means for communicating to provide low amplitude pressure oscillations to provide the low amplitude pressure oscillations in secretion loosening mode responsive to detecting the loosening trigger event, and for controlling the means for selectively controlling gas flow through the means for communicating to provide high amplitude pressure oscillations to provide the high amplitude pressure oscillations in the cough segmenting mode responsive to detecting the segmenting trigger event.

16. The system of claim 15, wherein means for detecting two or more trigger events is configured such that detecting the two or more trigger events comprises:
determining parameters of the gas flow based on the output signals, the parameters including one or more loosening parameters and one or more segmenting parameters;
obtaining threshold values for the one or more loosening parameters and the one or more segmenting parameters;
comparing the one or more loosening parameters to the threshold values for the one or more loosening parameters,
comparing the one or more segmenting parameters to the threshold values for the one or more segmenting parameters;
responsive to an individual loosening parameter breaching a corresponding threshold value for the individual loosening parameter, detecting the loosening trigger event; and
responsive to an individual segmenting parameter breaching a corresponding threshold value for the individual segmenting parameter, detecting the segmenting trigger event.

17. The system of claim 15, wherein the means for detecting the two or more trigger events is configured such that the two or more of the trigger events is detected responsive to receiving an indication of a manual action performed by the user.

18. The system of claim 15, wherein means for selectively controlling gas flow comprises a shunt valve configured to control whether the system provides low amplitude pressure oscillations or high amplitude pressure oscillations such that when the shunt valve is open, the system provides low amplitude pressure oscillations, and when the shunt valve is closed, the system provides high amplitude pressure.

19. The system of claim 15, wherein means for selectively controlling gas flow comprises a rotary valve configured to block and/or permit gas flow to provide the high amplitude pressure oscillations.

20. The system of claim 15, wherein means for selectively controlling gas flow includes a pressure generator configured to generate a bias pressure such that the loosening is performed with the bias pressure and the low amplitude pressure oscillations.

* * * * *